(12) United States Patent
Sato (10) Patent No.: US 7,569,365 B2
(45) Date of Patent: Aug. 4, 2009

(54) PROMOTER GENE, RECOMBINANT TURKEY HERPESVIRUS HAVING THE NOVEL PROMOTER GENE, AND POULTRY VACCINE INCLUDING THE RECOMBINANT HERPES VIRUS OF TURKEY

(75) Inventor: Takanori Sato, Fujisawa (JP)

(73) Assignee: Zeon Corporation, Tokyo (JP)

( * ) Notice: Subject to any disclaimer, the term of this patent is extended or adjusted under 35 U.S.C. 154(b) by 0 days.

(21) Appl. No.: 12/076,490

(22) Filed: Mar. 19, 2008

(65) Prior Publication Data

US 2008/0233146 A1 Sep. 25, 2008

(30) Foreign Application Priority Data

Mar. 20, 2007 (JP) ............................. 2007-073429

(51) Int. Cl.
*C12P 19/34* (2006.01)

(52) U.S. Cl. .................................. 435/91.1; 424/199.1

(58) Field of Classification Search .............. 424/199.1, 424/214.1, 192.1; 435/91.1
See application file for complete search history.

(56) References Cited

U.S. PATENT DOCUMENTS 5,961,982 A * 10/1999 Cochran ................... 424/199.1
6,632,664 B1 * 10/2003 Saitoh et al. .............. 435/320.1
7,153,511 B2 * 12/2006 Sato et al. ................. 424/199.1

* cited by examiner

*Primary Examiner*—Ali R. Salimi
(74) *Attorney, Agent, or Firm*—Kratz, Quintos & Hanson, LLP (57) ABSTRACT

Promoter genes that are derived from Marek's disease virus (MDV). These promoter genes can express two foreign genes when inserted in a recombinant turkey herpesvirus (HVT). A recombinant HVT having said novel promoter gene between two foreign genes. The poultry vaccine consisting of the recombinant turkey herpesvirus described in the present invention.

6 Claims, 5 Drawing Sheets

PROMOTER GENE, RECOMBINANT TURKEY HERPESVIRUS HAVING THE NOVEL PROMOTER GENE, AND POULTRY VACCINE INCLUDING THE RECOMBINANT HERPES VIRUS OF TURKEY

BACKGROUND OF THE INVENTION

1. Field of the Invention

The present invention relates generally to a novel promoter gene, which is derived from Marek's disease virus (MDV) and can express two foreign genes in a recombinant turkey herpesvirus (HVT). More specifically, the present invention provides a recombinant HVT having the novel promoter gene between the two foreign genes, at least one of which is derived from a pathogen of avian infectious disease, and a poultry vaccine consisting of the recombinant turkey herpesvirus.

2. Description of the Related Art

Virus-vectored vaccines such as recombinant fowl pox viruses (FPV) or recombinant HVT have been already used in the poultry industry in the USA. In particular, live HVT vaccine is safe and efficacious against Marek's disease, and can be injected in ovo, which is suitable for mass vaccination of poultry flocks.

Because HVT is propagated through cell-to-cell infection, it is relatively free from the influences of anti-HVT specific antibodies present in the circulating blood. Therefore, the HVT live vaccine has a good character exhibiting its full effect even in the case of the presence of maternal antibody, which often attenuates the efficacy of a live vaccine.

It is well known that the genus herpesvirus, which includes HVT, has a property of permanently surviving in the body of an infected animal in the state of latent infection or persistent infection, and as a result, herpesvirus has the excellent vaccine character that it can raise a long duration immunity to a immunized animal.

Recombinant HVT vaccines have been reported (Japanese Patent No. 3587065, U.S. Pat. No. 7,153,511). Recombinant HVTs (HF006 and HF007) having multiple foreign genes such as HN and F genes derived from Newcastle disease virus (NDV), and VP2 gene derived from Infectious bursal disease virus (IBDV) were described in Japanese Patent No. 3587065, and they can express these foreign genes and elicit immunity to vaccinated chickens.

However, these recombinant HVT expressing multiple foreign genes were in most cases unstable, and all or a part of the foreign genes inserted in their genome are deleted during repeating passaging in culture cells.

As a result of intensive study to solve the above problems, the inventors of the present invention have found that bi-directional promoters derived from MDV can be useful for recombinant HVT, and that a recombinant HVT that is an HVT into the genome of which an expression cassette comprising two different foreign genes under control of the bi-directional promoter is inserted, can be very stable, such that the inserted foreign genes are not deleted, and are useful for poultry vaccines.

DETAILED DESCRIPTION OF THE INVENTION

In one embodiment, the present invention is a novel bi-directional promoter gene that is derived from MDV and that can express two foreign genes in a recombinant HVT.

In another embodiment, the present invention provides a recombinant HVT, into the genome of which an expression cassette comprising two different foreign genes under control of the bi-directional promoter is inserted. A specifically preferred insertion site for an expression cassette is at least one insertion site selected from the group consisting of sites in between UL45 and UL46.

In the present invention, the term "recombinant" will refer to recombinant DNA technology, also called gene cloning or molecular cloning, which refers to techniques of transfer of DNA from one organism to another. The term "recombinant herpesvirus of turkeys" will here refer to an existing herpesvirus of turkeys whose genome has been modified by insertion of DNA from another source. It will be understood that the resulting "recombinant herpesvirus of turkeys" can be manufactured by a variety of methods, and once made, can be reproduced without use of further recombinant DNA technology. The structure of the "recombinant herpesvirus of turkeys" is therefore described in terms of DNA insertion, that is, of a method of making it.

In one embodiment, at least one of the above two foreign genes is derived from a pathogen of avian infectious diseases, and in particular, is an antigen gene derived from a pathogen selected from the group consisting of viruses, bacteria, fungi, and protozoa.

In another embodiment, the present invention is a poultry vaccine comprising the above recombinant virus as an active ingredient.

The present invention will now be explained herein below in more detail.

(Turkey Herpesvirus)

As long as it is non-pathogenic to chickens, any HVT can be used in the present invention. For instance, the following HVT strains, FC126 (ATCC VR-584B), PB-THV1, H-2, YT-7, WTHV-1, and HPRS-26, are suitable for the backbone virus. Among these, the FC126 strain is favorable for use in the present invention.

(Marek's Disease Virus (MDV))

Any MDV can be used as a source of bi-directional promoter gene in the present invention. Strains as used as a vaccine are preferable, and specific examples of it include CVI988, and SB1 strains.

(Promoter)

Promoters are generally known in biology as sites on DNA to which the enzyme RNA polymerase can bind and initiate the transcription of DNA. In the present invention, the terminology that a gene in the recombinant HVT is "under control of a promoter" means that, when the recombinant HVT infects a cell, there is enhanced expression of the gene compared to the expression by the corresponding virus where the promoter is not present.

In the present invention, the promoter gene derived from MDV has bi-directional transcription activity to express both of two different foreign genes. A promoter gene DNA cloned from MDV genome could be modified by deleting a part of it as long as the promoter activity is functional in cells or in the bodies of avian species.

One method of identifying bi-directional promoter genes is to identify two open reading frames (ORFs) that are mutually counter direction, from MDV genomic information, and the intergenic region among the two ORFs is a candidate for a bi-directional promoter gene. The below examples illustrate the identification of such promoters.

The promoter of the present invention may be less than 1 kbp long, and in particular, may be less than 800 bp long. Shorter promoters are often more stable in the recombinant HVT.

Examples of such promoter genes are SEQ ID NO: 1, which corresponds to nucleotides 91,827 to 92,296 of MDV genomic DNA (Acc #: AF243,438), and SEQ ID NO: 2, which corresponds to nucleotides from 98,757 to 99,412 of MDV genomic DNA (Acc #: AF243,438).

In one embodiment of the invention, when different restriction enzyme sites are introduced into 5' and 3' ends of the promoter gene cloned from MDV genome, two different foreign genes can be set easily in the front of and after the promoter gene. Examples of such modified promoter genes include the sequence from nucleotide 19 to 60 of SEQ ID NO: 19, and the sequence from nucleotide 60 to 768 of SEQ ID NO: 22.

(Expression Cassette)

The inserted genes of the present invention are inserted into recombinant HVT genome as the expression cassette comprising two different foreign genes under control of a promoter derived from MDV. The number of the inserted expression cassettes is not limited but the length of the inserted expression cassette (if multiple cassettes, the total length) is preferably less than 10 kbp long because of the stability of the recombinant HVT.

The foreign genes in the expression cassette may be any genes as long as they are not originally derived from HVT genome and are not expression regulatory genes. In the poultry vaccines of the invention, the foreign genes are preferably antigen genes derived from a pathogen of avian infectious diseases.

Examples of pathogens that cause infection in avian include virus, bacteria, fungi, protozoa, etc. Specific examples of such pathogens include New castle disease virus (NDV) and Infectious bursal disease virus (IBDV), Infectious laryngotracheitis virus (ILTV), Infectious bronchitis virus (IBV), *Mycoplasma* (MG).

Specifically, it is most preferable that neutralizing antigens or the genes of antigens that are considered immunoprotective antigens are used as foreign genes, because the recombinant viruses would be effective vaccines.

Examples of such antigen genes, HN protein, F protein, and NP protein for NDV, and M protein, N protein, and spike protein for IBV, VP2 protein for IBDV, gB protein for ILTV, 40K protein, 66K protein, and 67K protein (sequences are described in International Patent Publication WO 94/23019), etc., for *Mycoplasma*.

Besides antigen genes, marker protein genes may be preferably used as foreign genes. Examples of marker genes include green fluorescence protein derived from *Aequorea victoria*, and enzymes such as beta-galactosidase derived from *Escherichia coli*.

Figure 1:
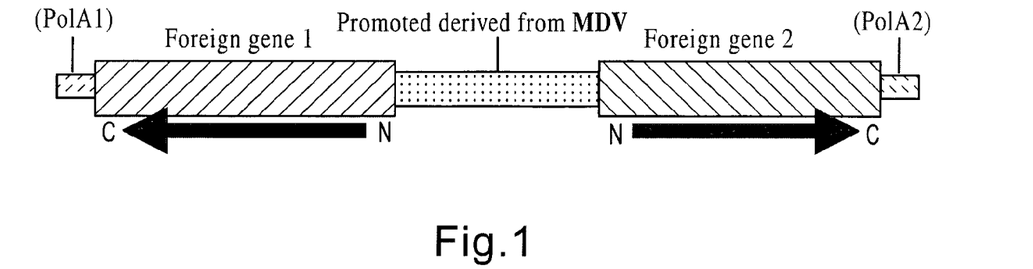
FIG. 1 Conceptual diagram of the expression cassette.

The expression cassette of the present invention comprises two different foreign genes under control of a promoter derived from MDV as mentioned above, and besides, it is most preferable that short terminal sequences comprising polyadenylation (poly(A)) signal and restriction enzyme sites are included in the end of the expression cassette (FIG. 1). The short terminal sequences may be less than 100 bp long, in particular less than 50 bp; shorter sequences tend to be more stable in the recombinant HVT. Examples of the short terminal sequences are SEQ ID NO: 3 and SEQ ID NO: 4.

(Construction of rHVT)

For the present invention, any known method of generating recombinant HVT is applicable, and examples of known methods were reported in *Avian Disease* (1992) 36: 858-870 and in examples of U.S. Pat. No. 6,632,664.

A typical example of the present invention is as follows. (1) First, a recombinant plasmid that contains a non-essential region of the HVT genome is constructed. Then, more than one expression cassette is inserted into the non-essential region to generate a homology vector (a plasmid containing the expression cassette). (2) The homology vector is transfected into chicken embryo fibroblast (CEF) cells infected with parent HVT or co-transfected into CEF cells with infectious HVT genomic DNA. Transfection can be performed by any known method. (3) The transfected CEF cells are planted on tissue culture plates and incubated until virus plaques become visible. (4) The identifiable plaques include recombinant virus as well as parent wild-type virus. The recombinant virus may be purified from wild type virus by any known method to detect expression of foreign genes in the expression cassette.

For the above recombinant plasmid, any plasmid is applicable, and examples include plasmids such as pBR322, pBR325, pBR327, pBR328, pUC18, pUC19, pUC7, pUC8, and pUC9, and cosmids such as pHC79.

In the present invention, one more expression cassette is inserted into a non-essential region of the HVT DNA genome. For instance, the expression cassette can be inserted into, but not limited to inter-ORF region between UL44 and UL46 (U.S. Pat. No. 6,632,664), most preferably, the inter-ORF region between UL45 and UL46.

(Poultry Vaccine Consisting Mainly of the Recombinant Turkey Herpesvirus)

The vaccine, consisting mainly of the recombinant HVT in the present invention, may also include chicken cells and/or ingredients of culture media. As long as not pharmacologically detrimental, the vaccine may contain any ingredients such as preservatives. In addition, the vaccine of the present invention can be used in a mixture with any recombinant or non-recombinant viruses such as the MDV serotype 1 or serotype 2 vaccine strains.

The vaccine of the invention will generally include the recombinant HVT and an additional component, such as a pharmaceutically acceptable carrier, excipient or adjuvant. It may, of course, have more than one of these additional components present.

Any known method is applicable to the preparation of the recombinant vaccine in the present invention. For instance, the recombinant HVT may be inoculated into permissive culture cells such as CEF cells and grown to an appropriate titer. Then, the cells are removed from tissue culture plates or roller bottles with cell scrapers or by trypsin treatment and collected by centrifugation. The pelleted cells are then suspended in culture medium containing dimethyl sulfoxide (DMSO), frozen slowly, and then stored in liquid nitrogen.

The poultry vaccine of the present invention can be administered to chickens by any known method of inoculating Marek's disease vaccine. For instance, the vaccine of the present invention is diluted to give $10^1$-$10^5$, or more favorably $10^2$-$10^4$ plaque forming units (pfu) per dose, and inoculated subcutaneously behind the neck of one-day-old chicks or into embryonating eggs via the in ovo route with syringes or with any apparatus for injection.

The poultry vaccine of the present invention is sometimes used as multiple value-vaccine not only against Marek's disease but also against the disease from which inserted foreign gene is derived.

EXAMPLES

Gene cloning and plasmid construction was essentially performed by the standard molecular biology techniques (*Molecular Cloning: A Laboratory Manual*. 3rd Edition, Cold Spring Harbor Laboratory Press, Woodbury, N.Y. 2001). The turkey herpesvirus FC126 strain (R. L. Witter et al., 1970, *Am. J. Vet. Res.* 31, 525-538) was used as a backbone virus to generate a recombinant turkey herpesvirus.

Example 1

Cloning of Bi-Directional Promoters Derived from MDV

The genome structure of MDV was reported by Tulman et al. (*J. Virol.* (2000) 74: 7980-7988), but the positions or activities of almost promoters on the genome have not been clear. There were only two papers about analysis of transcripts from UL41 to UL51 (*J. Gen. Virology* (1998) 79: 1997-2001), and from UL30 to UL40 (*J. Gen. Virol.* (1999) 80: 2417-2422) by Izumiya et al. Two bi-directional promoter candidates were selected using data from the above three reports. One was a DNA region corresponding to nucleotide 91,827 to 92,196, and the other was the sequence corresponding to nucleotide 98,757 to 99,412, of the MDV genome sequence reported as Genebank Acc. #: AF243438.

MDV CVI988 strain (a commercial MDV vaccine) was infected into CEF cells in a 150-mm dish and propagated. The infected cells were washed with PBS, lysed with 4ml of lysis buffer (0.5% sodium dodecyl sulfate (SDS), 100 mM NaCl, 1 mM EDTA, 200 µg/ml protenase in 10 mM Tris (pH8.0)) and incubated at 37° C. for 4 hrs. The lysate were transferred to a 50-ml tube (FALCON), and an equal volume of TE-saturated phenol was added. The tube was inverted slowly for 15 min, and centrifuged at 1500×g for 5 min. The aqueous layer was transferred to a new tube. An equal volume of chloroform: isoamyl alcohol (24:1) was added, and mixed gently. The tube was centrifuged at 1500×g. for 5 min. The aqueous layer was transferred to a new tube. Two-times volume of 100% ethanol was added, and mixed gently. The tube was centrifuged at 1500×g for 5 min. The precipitates were rinsed with 70% ethanol, dried and suspended with 0.1 ml of TE. This solution included MDV genome DNA.

Using the prepared DNA as a template, the DNA fragment corresponding to nucleotides 91,709 to 92,261 of the MDV genome (Acc. #: AF243438) was amplified by polymerase chain reaction (PCR) with the PCR primer set of MD50F (SEQ ID NO: 5) and MD51R (SEQ ID NO: 6). The amplified 553-base DNA fragment was ligated into pPCR SCRIPT AMP vector (Stratagene, Cat. #211188), and *E. coli*-competent JM109 cells were transformed with the ligation mixture. Several transformants were checked, and insert DNA from three candidate plasmids were sequenced. Two of three insert DNAs were completely identical (SEQ ID No. 7), and the corresponding plasmid was named as pPCR-Pmd50.

In a similar way, the DNA fragment corresponding to nucleotides 98,715 to 99,464 of the MDV genome was amplified by PCR using the primer set of MD54F (SEQ ID NO: 8) and MD55R (SEQ ID NO: 9) and inserted into pPCR SCRIPT AMP vector. The insert DNAs of three candidate plasmids were found to be completely identical (SEQ ID NO: 10), but these differed in sequence by one base from the corresponding sequences of Acc. #: AF243438. The plasmid was named as pPCR-Pmd54.

Example 2

Modification of Promoters Derived from MDV

The synthetic DNA adapter formed by annealing Ad_Kp-Bg-SaU (SEQ ID NO: 11) and Ad_Kp-Bg-SaL (SEQ ID NO: 12) was inserted into each of pPCR-Pmd50F or pPCR-Pmd54F cut with KpnI, and subsequently with SalI. The resulting plasmids were named as pPmd50M1 or pPmd54M1, respectively.

The synthetic DNA adapter formed by annealing Ad_No-Sf-SaU (SEQ ID NO: 13) and Ad_No-Sf-SaL (SEQ ID NO: 14) was inserted into each of pPmd50M1 or pPmd54M1 cut with SacI, and subsequently with NotI. The resulting plasmids were named as pPmd50M2 or pPmd54M2, respectively.

After that, the synthetic DNA adapter formed by annealing Ad_Nc-Bg-Xh-NoU (SEQ ID NO: 15) and Ad_Nc-Bg-Xh-NoL (SEQ ID NO: 16) was inserted into each of pPmd50M2 or pPmd54M2 cut with NcoI and with NotI. The resulting plasmids were named as pPmd50M3 or pPmd54M3, respectively.

PCR was conducted using pPCR-Pmd50 as a template and with the primer set of Pmd50F (SEQ ID NO:17) and Pmd51R (SEQ ID NO: 18). The amplified PCR product was cut with BamHI and with NcoI, and the resulting DNA of about 380 bp was inserted into pPmd50M3 cut with BamHI and NcoI, resulting in pPmd50F. The nucleotide sequences of multi-cloning sites from KpnI site to SacI site of pPmd50F were confirmed by sequencing (SEQ ID NO: 19).

In a similar way, PCR was conducted using pPCR-Pmd54 as a template and with the primer set of Pmd54F (SEQ ID NO: 20) and Pmd55R (SEQ ID NO: 21). The amplified PCR product was cut with BamHI and with NcoI, and the resulting DNA of about 670 bp was inserted into pPmd54M3 cut with BamHI and NcoI, resulting in pPmd54F. The nucleotide sequences of multi-cloning sites from KpnI site to SacI site of pPmd54F were confirmed by sequencing (SEQ ID NO: 22).

Example 3

Construction of Expression Cassettes Comprising Two Different Foreign Genes Under Control of a Promoter Using the commercial plasmid pGFP (CLONTECH, Cat. #: 6097-1) having the GFP protein gene of *Aequorea victoria* as a template, PCR was conducted with the primer set of GFPBspF (SEQ ID NO: 23) and GFPSa1R (SEQ ID NO: 24). The amplified PCR product was cut with BspHI and SalI, and the resulting DNA was inserted into pPmd50F cut with XhoI and NcoI, resulting in pPmd51GFP.

Figure 2:
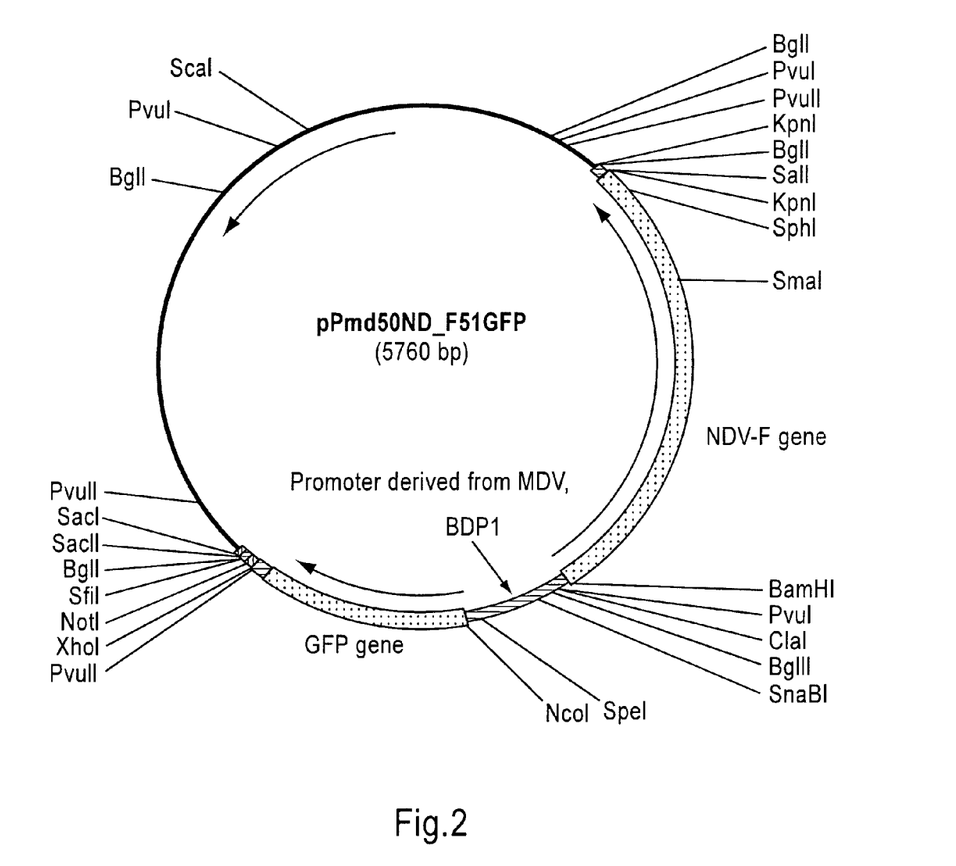
FIG. 2 Illustration of the plasmid containing expression cassette pPmd50ND_F51GFP.

The NDV F gene was prepared from pRSV-F (described in EXAMPLE 7 of U.S. Pat. No. 6,632,664) by digesting with BamHI and SalI, and inserted into pPmd51GFP cut with BamHI and SalI, resulting in pPmd50ND_F51GFP (FIG. 2), which is the plasmid containing a expression cassette comprising GFP gene, NDV F gene, and a promoter (BDP1: SEQ ID NO: 1) which was derived from MDV and set between GFP and F genes.

Using the plasmid p45/46bacVP2-E (described in U.S. Pat. No. 7,153,511) as a template, PCR was conducted with the primer set of BspVP2-F (SEQ ID NO: 25) and VP2 Xho-R (SEQ ID NO: 26). The amplified PCR product, IBDV VP2 gene of about 1.4 kbp, was cut with BspHI and XhoI, and the resulting DNA was inserted into pPmd54F cut with XhoI and NcoI, resulting in pPmd55IBD_VP2.

Figure 3:
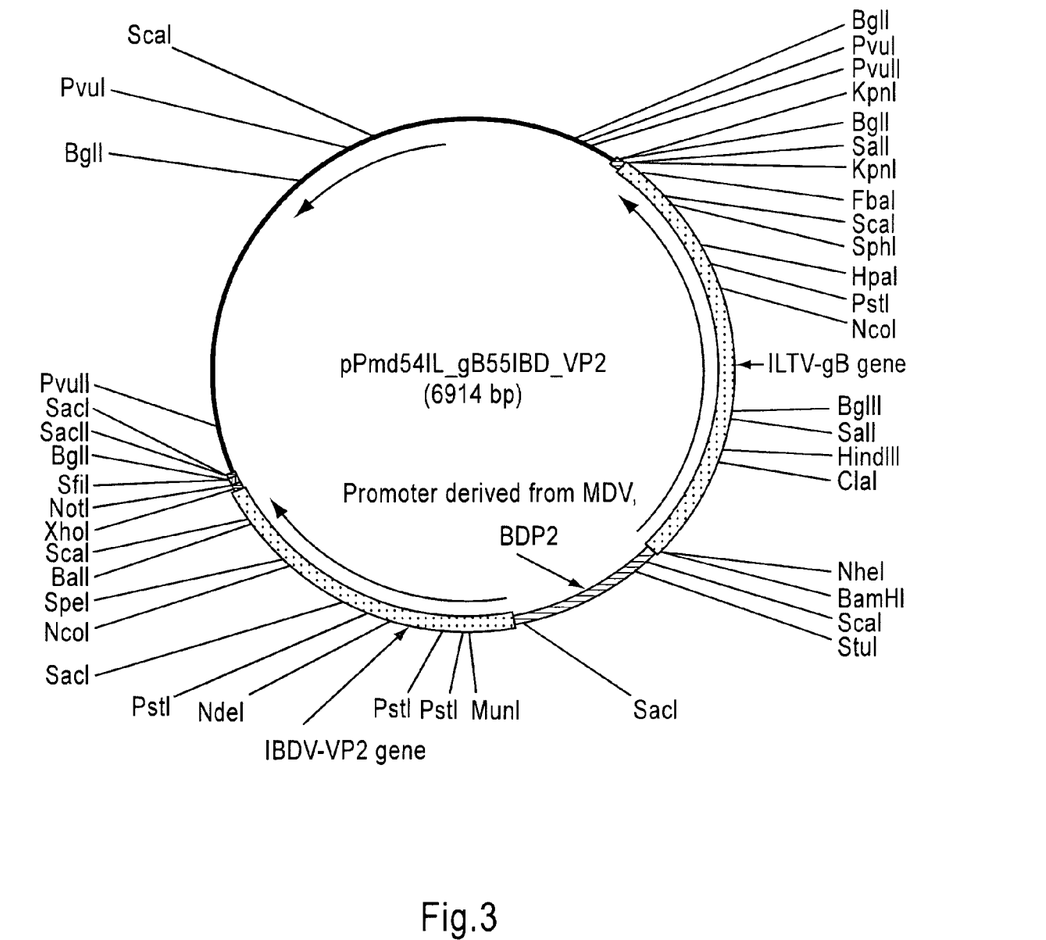
FIG. 3 Illustration of the plasmid containing expression cassette pPmd54IL_gB55IBD_VP2.

The ILTV gB gene of about 1.9 kbp was prepared from p45/46PecILgBdellac+STP (described in WO2005/093070) by digesting with BamHI and SalI, and inserted into pPmd55IBD_VP2 cut with BamHI and SalI, resulting in pPmd54IL_gB55IBD_VP2 (FIG. 3), which is the plasmid containing a expression cassette comprising ILTV gB gene, IBDV VP2 gene, and a promoter (BDP2: SEQ ID NO: 2) which was derived from MDV and set between gB and VP2 genes.

Example 4

Construction of a Homology Vector to Make a Recombinant HVT

HVT genomic DNA was prepared according to the method described in EXAMPLE 1 of U.S. Pat. No. 6,632,664 and used as a template for PCR that was conducted with a primer set of HVT45Sph (SEQ ID NO: 27) and HVT46Xho (SEQ ID NO: 28). The amplified PCR product of about 1.0 kbp was digested with SphI and XhoI and inserted into pNZ45/46BacpA (described in U.S. Pat. No. 7,153,511) cut with SphI and XhoI, resulting in the plasmid p46.

Figure 4:
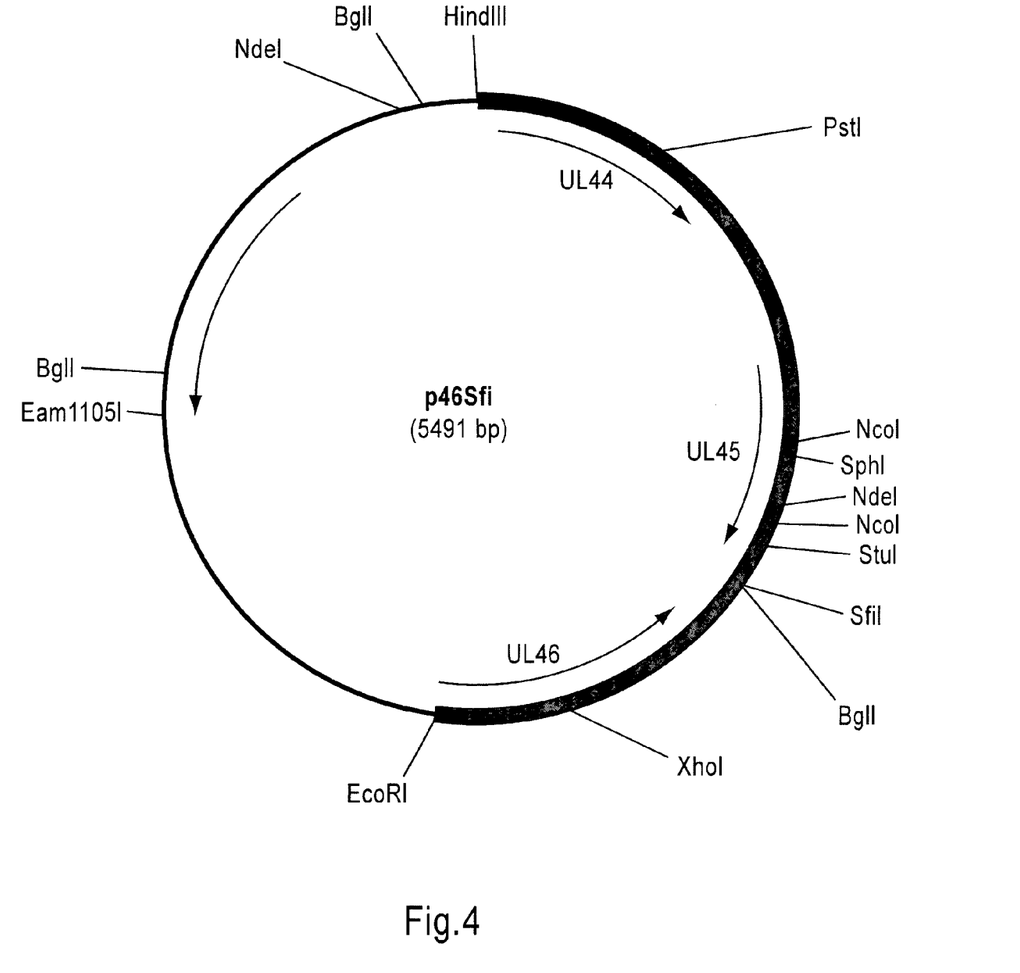
FIG. 4 Illustration of the recombinant plasmid containing a non-essential region of HVT DNA, p46Sfi.

Using p46 as a template, PCR was conducted with two primer sets [one: HVT45Sph (SEQ ID NO: 27) and 45SfiR (SEQ ID NO: 29) and the other: 46SfiF (SEQ ID NO: 30) and HVT46Xho (SEQ ID NO: 28)]. PCR products of about 0.4 kbp and 0.6 kbp were amplified, respectively. They were separated from excess primers, and mixed, denatured and allowed to reanneal for use in the following PCR as templates. The following PCR was conducting with outside primers (HVT45Sph and HVT46Xho) to generate SfiI site. The resulting PCR product of about 1.0 kbp was digested with SphI and XhoI and inserted into p46 cut with SphI and XhoI, resulting in p46Sfi (FIG. 4).

The plasmid pPmd50ND_F51GFP was digested with BglI and the expression cassette of about 3.1 kbp was recovered from an agarose gel. The cassette was inserted into p46Sfi cut with SfiI, resulting in p46md50ND_F51GFP.

Figure 5:
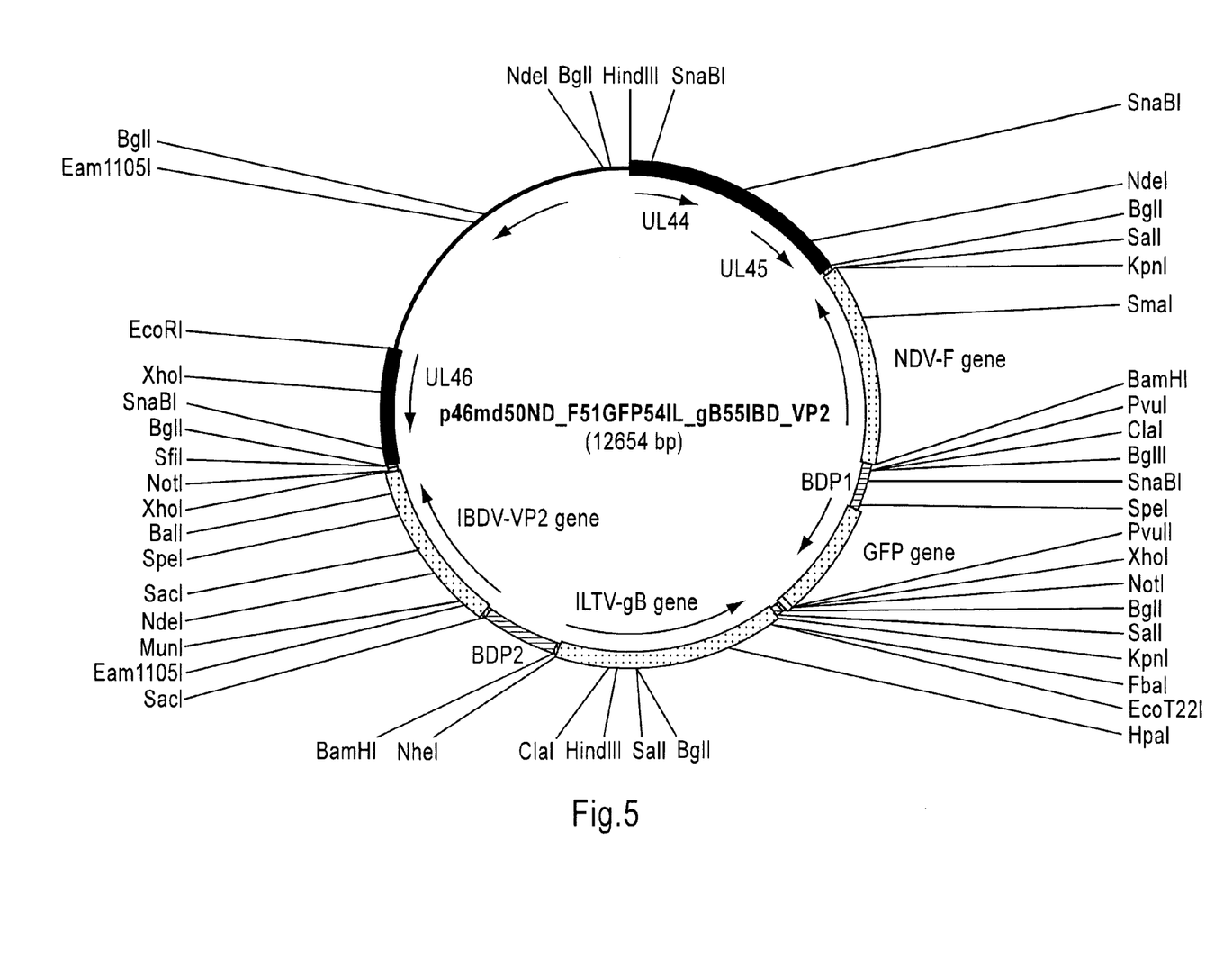
FIG. 5 Illustration of the homology vector for FW101, p46md50ND_F51GFP54IL_gB55IBD_VP2.

Then, the plasmid pPmd54IL_gB55IBD_VP2 was digested with BglI and the expression cassette of about 4.0 kbp was recovered from an agarose gel. The cassette was inserted into p46md50ND_F51GFP cut with SfiI, resulting in p46md50ND_F51GFP54IL_gB55IBD_VP2 (FIG. 5), which a homology vector having two expression cassettes to make a recombinant HVT.

Example 5

Generation and Isolation of Recombinant Turkey Herpesvirus (FW101)

Viral DNA of the HVT FC126 strain was prepared as described in EXAMPLE 1 of U.S. Pat. No. 6,632,664.

$10^7$ secondary chicken embryo fibroblast (CEF) cells were suspended in Saline G (0.14 M NaCl, 0.5 mM KCl, 1.1 mM $Na_2HPO_4$, 1.5 mM $NaH_2PO_4$, 0.5 mM $MgCl_2$, and 0.011% glucose) and co-transfected with 15 µg of HVT viral DNA and 25 µg of p46md50ND_F51GFP54IL_gB55IBD_VP2 (EXAMPLE 4) by electroporation. Electroporation was performed using BIO-RAD GENE PULSER. Transfected cells were incubated for 10 minutes at room temperature and transferred to wells of 96-well plates. These were incubated at 37° C. for 7 days in 4-5% $CO_2$, or until the plaques became visible.

Using an inverted microscope (IX70: OLYMPUS Corp., Japan) with fluorescence imaging (IX-FLA: OLYMPUS), visible virus plaques were observed to detect expression of GFP protein. Wells containing plaques expressing GFP protein were identified, and cells were trypsinized, then diluted in fresh secondary CEF cells and transferred to another 96-well plate. The purification procedure was repeated until all plaques express GFP protein using the microscopy with fluorescence imaging. CEF cells of positive wells were trypsinized, diluted in fresh secondary CEF cells and transferred to one well of a 6-well plate. When confluent plaques were visible in the well, infected CEF cells were recovered by trypsin, suspended with 2 ml of SPGA-SBT buffer (7.46 g sucrose, 5.2 mg $KH_2PO_4$, 125.4 mg $K_2HPO_4$, 91.7 mg L-glutamine, 1 g Bovine serum albumin, 10 g sorbitol in 100 ml), and transferred to a tube (EPPENDORF). The tube was set in a sonication machine (BIOSONIC; Sanko-Jyunyaku, Japan).

The infected cells in the tube were ultrasonicated and centrifuged at 1,000×g for 5 min. Extracellular HVT was transferred to a new tube, and diluted serially with SPGA-SBT. Aliquots (40 µl) of the diluted extra cellular HVT were transferred to each well of 96-well plates in which fresh secondary CEF cells were grown and medium cultures were recently removed. Two hours after infection, 200 µl of medium were added into each well of the 96-well plates. The 96-well plates were incubated until plaques were visible. The HVT plaques were observed using the inverted microscope with fluorescence imaging to select a well in which there was only one positive plaque. The HVT plaque in the well was completely purified, and the purified recombinant HVT was designated as FW101.

Example 6

Verification of Genome Structure and Stability of Recombinant HVT 6-1. Southern Blot Analysis Chicken embryo fibroblast cells grown in a 150-mm dish, that were infected with the recombinant virus, FW101 (obtained in EXAMPLE 5), or the HVT FC126 parent strain, were used in a Southern blot analysis to confirm the genome structure of the recombinant HVT. The cells were collected by a cell scraper and by centrifugation at 500×g for 5 minutes. The harvested cells were washed with phosphate buffered saline (PBS) and resuspended in 2.0 milliliter (ml) of lysis buffer (0.5% TRITON X-100 (non-ionic surfactant), 100 mM 2-mercaptethanol, and 20 mM EDTA in PBS). The cell suspension was vortexed for a total of 30 seconds and incubated for 15 minutes at room temperature. Cell nucleus and cell debris were removed by centrifuging at 2,060×g for 5 minutes and the supernatant was transferred to a 1.5-ml tube. Viruses were collected by centrifugation at 20,800×g for 20 minutes at 22° C. The pellet was suspended in 0.33 ml of a nuclease solution (12.5 mM Tris-Cl (pH7.5), 1 µg/ml DNase I and 1 µg/ml RNase A) and incubated at 37° C. for 30 minutes. Then, 83 µl of SDS-protease solution (50 mM EDTA, 5% SDS, 0.5 mg/ml protease K, and 25 mM 2-mercaptoethanol) was added to the virus suspension and incubated at 55° C. for 30 minutes to disrupt virus envelopes. Phenol/chloroform extraction was conducted twice and DNA was precipitated by adding 2.5 volumes of cold 100% ethanol and NaCl at a final concentration of 0.16 M. After centrifuging at 20,800×g for 30 minutes at 4° C., the pellet was washed with 70% ethanol and air-dried. The pellet was dissolved in TE buffer (10 mM Tris-Cl (pH 8.0), and 1 mM EDTA).

The viral DNA in TE buffer and the homology vector (positive control) were digested with XhoI, BamHI and SpeI and separated by agarose gel electrophoresis using 0.6% agarose gel. DNA fragments on the gel were transferred to a BIODYNE A nylon membrane (Pall Corporation, Cat #BNXF3R). The membrane was hybridized with either Digoxigenin (DIG)-labeled VP2 probe or DIG-labeled IS45/46 probe. The DIG-labeled VP2 probe and the IS45/46 probe were prepared with PCR DIG Probe Synthesis Kit (Roche Applied Science, Cat #11636090910) using primers VP2-F (SEQ ID NO: 31) and VP2-R (SEQ ID NO: 32) and primers 45/46-F (SEQ ID NO: 33) and 45/46-R (SEQ ID NO: 34), respectively.

The membrane was washed with 2×SSC solution at room temperature and then with 0.5×SSC solution at 68° C. The membrane was blocked and incubated with anti-Digoxigenin-AP, Fab fragments (Roche Applied Science, Cat #11093274910) for 30 minutes at room temperature. After washing two times with maleic acid washing buffer (0.1 M maleic acid, 0.15 M NaCl, and 0.3% TWEEN20 (non-ionic detergent), pH 7.5), DNA bands that were hybridized with the probes were visualized by incubating the membrane with BCIP/NBT solution. The VP2 probe hybridized with 2.0 kb bands in the recombinant virus DNA and the homology vector, while no bands were detected with the HVT parent. The IS45/46 probe hybridized with 1.7 kb and 0.6 kb bands in the recombinant DNA and the homology vector. These results demonstrated that FW101 obtained in EXAMPLE 5 had the expected genomic structure.

6.2. Stability of FW101

The recombinant virus FW101 was passaged 20 times blindly in CEF cells. After the 20 passages, the virus was analyzed by the Southern blot analysis as described in EXAMPLE 6.1. Bands detected in DNA isolated from the virus after 20 passages were identical to the bands described in EXAMPLE 6.1, demonstrating that the recombinant virus was stable even after 20 passages.

Example 7

Protein Expression by FW101

1.1. Fluorescent Antibody (FA) Method

Expression of NDV-F and IBDV-VP2 proteins in FW101-infected CEF cells was confirmed according to the method described in EXAMPLE 16 of U.S. Pat. No. 6,632,664.

1.2. Western Blot Assay

To confirm expression of the IBDV-VP2 protein by FW101, the western blot was conducted using CEF cells infected with FW101 and Mouse monoclonal antibody (Mab) R-63 (Hybridoma cells expressing this Mab were purchased from ATCC Cat. #: HB-9490). Briefly, CEF cells in 100-mm dishes were infected with FW101 or the parent HVT FC126 strain at a multiplicity of infection of approximately 0.01. Three days post inoculation, cells were harvested with cell scrapers and centrifuged at 913×g for 5 minutes. The pellet was washed with PBS twice and resuspended with 50 to 100 μl of PBS. After adding the same volume of 2× SDS sample buffer (130 mM Tris-Cl (pH6.8), 6% SDS, 20% glycerol, 10% 2-mercaptoethanol and 0.01% bromophenol blue), cell suspension was boiled for 5 minutes. The samples were separated by SDS-PAGE using 10% polyacrylamide gel and transferred to a PVDF membrane (IMMOBILON-P (MILLIPORE)). The membrane was dried completely and then incubated with Mab R-63 or Mab JL-8 against GFP (purchased from CLONTECH). A protein band of 40 kilodaltons (kDa) or 26 kDa was observed only in the lane with FW101 infected cells, which was the expected size of the VP2 or GFP protein, respectively.

Example 8

Serological Evaluation of Chickens Inoculated with FW101

Serological responses in chickens that were vaccinated with FW101 were evaluated. One-day-old specific pathogen free chicks (NIBS, Oume, Japan) were vaccinated subcutaneously with 3000 pfu per dose (0.1 ml) of either FW101 or wild HVT. Chickens were bled between 1 to 6 weeks old and obtained sera were evaluated by the IBD ELISA kit (Gen Corp., Japan). The S/P values of ELISA results were shown in TABLE 1. As shown in TABLE 1, sera from chickens vaccinated with FW101 started to show positive S/P value as early as two weeks post vaccination, which indicated that FW101 was useful as a poultry vaccine.

TABLE 1

Time course of anti-VP2 antibodies in immunized chickens

| Immunized | S/P Value (wpi: week post immunization) | | | | | | |
|---|---|---|---|---|---|---|---|
| virus | 0 wpi | 1 wpi | 2 wpi | 3 wpi | 4 wpi | 5 wpi | 6 wpi |
| FW101 | 0.0 | 0.0 | 0.14 | 0.28 | 0.30 | 0.22 | 0.25 |
| Wild HVT | 0.0 | 0.0 | 0.0 | 0.0 | 0.0 | 0.0 | 0.0 |

---

What is claimed is:

1. A recombinant turkey herpesvirus, made by inserting, into a turkey herpesvirus, an expression cassette comprising two different foreign genes under control of a promoter derived from Marek's disease virus,
   wherein the nucleotide sequence of said promoter is SEQ NO. 1 or SEQ NO. 2.

2. A recombinant turkey herpesvirus as in claim 1, wherein said expression cassette is inserted into the site between UL45 and UL46 of the turkey herpesvirus genome.

3. A recombinant turkey herpesvirus as in claim 1 or claim 2, wherein at least one of said two different foreign genes is an antigen gene derived from a pathogen of avian infectious diseases.

4. A poultry vaccine comprising:
   the recombinant turkey herpesvirus as in claim 3; and
   at least one of a carrier, an excipient, and an adjuvant.

5. A nucleic acid whose sequence is SEQ NO. 1.

6. A nucleic acid whose sequence is SEQ NO. 2.

* * * * *

SEQUENCE LISTING

<160> NUMBER OF SEQ ID NOS: 34

<210> SEQ ID NO 1
<211> LENGTH: 370
<212> TYPE: DNA
<213> ORGANISM: Marek's disease gammaherpesvirus

<400> SEQUENCE: 1

```
tattcaggca actatcgcca accctctgtt ctccctagat gcgatcgata ttagaaagat      60
ctataaaatg taatacggct ttcaatacca caactcctaa aaccagtcgt gattacgtag     120
tatagtcatg cccatttcag agaacataca ataacacagt aaaatcctac taaatattgt     180
```

-continued

```
atctgcacta ttacttgacc atgccagagt aaatcgtcat ttctattatc gccacacaaa        240
cgacagcaat acataatacg cctcaaccca acgtaatatc tgcaatatcg gagttattta        300
cagccattgc cgaacacggg acagtatttt tactagtagc taatttcgat ttccgtcaat        360
tatctacatc                                                              370

<210> SEQ ID NO 2
<211> LENGTH: 656
<212> TYPE: DNA
<213> ORGANISM: Marek's disease gammaherpesvirus

<400> SEQUENCE: 2
gatgaccctc gcagttttta aatataacct aaatagaaac ctgaaattat cacaagtact         60
acagttctgt cagatatatc ctaactccta ataacaaagt acacgtgaaa taggcctaac        120
agtgaaacga tactcggt tactacatta aaatattaat cggaattaca cttctgaagg         180
atctggttca tgtaaatctt aaccattcta tatagcaata tacggattct atattgtctt        240
ataaataagt aaattgcatg ttttaaccta taattaactc gttataggta gacatgactc        300
atactagggt tgatttgcac atagcttagc cagatgcagt aaatatattg tcacgtggct        360
aaaacgtgag tagtaactta tatggcgaat taaacttata tccaatggcg ttcgcggacc        420
ttcacacgga aacatgtgtg gtgcgacatt caagtggtta tgagcgtcag ttgaacgtag        480
aacatgcgca ttgcaattat gtcccagaat cctcccccat ataaattcgt ctactgaaat        540
tcaagagcac ttgctgtatt acttccactt cgacgaacaa cacacaagac cagtcagccg        600
cgaacggaaa taacgccgaa tcgagctcct ctaattccga taaccggctg ttgtca          656

<210> SEQ ID NO 3
<211> LENGTH: 27
<212> TYPE: DNA
<213> ORGANISM: Artificial Sequence
<220> FEATURE:
<223> OTHER INFORMATION: Artificial polyA signal

<400> SEQUENCE: 3
cccagcatac ctaaataaat aaaaagc                                            27

<210> SEQ ID NO 4
<211> LENGTH: 17
<212> TYPE: DNA
<213> ORGANISM: Artificial Sequence
<220> FEATURE:
<223> OTHER INFORMATION: Artificial polyA signal

<400> SEQUENCE: 4
ctaaataaat aaaaagg                                                       17

<210> SEQ ID NO 5
<211> LENGTH: 27
<212> TYPE: DNA
<213> ORGANISM: Marek's disease gammaherpesvirus

<400> SEQUENCE: 5
cctccgcggt tgcagtagca ccccatg                                            27

<210> SEQ ID NO 6
<211> LENGTH: 25
<212> TYPE: DNA
<213> ORGANISM: Marek's disease gammaherpesvirus
```

<400> SEQUENCE: 6
ccgttcagcg tgtcaggata cagac                                        25

<210> SEQ ID NO 7
<211> LENGTH: 553
<212> TYPE: DNA
<213> ORGANISM: Marek's disease gammaherpesvirus

<400> SEQUENCE: 7
cctccgcggt tgcagtagca ccccatggtt ctgtcggcga cgttctcgaa gataaggacc    60
gtagcgtgtc caataaaact ttcagtggcc atatttcatc ggtcgttacg gcagacatta   120
ttcaggcaac tatcgccaac cctctgttct ccctagatgc gatcgatatt agaaagatct   180
ataaaatgta atacggcttt caataccaca actcctaaaa ccagtcgtga ttacgtagta   240
tagtcatgcc catttcagag aacatacaat aacacagtaa aatcctacta aatattgtat   300
ctgcactatt acttgaccat gccagagtaa atcgtcattt ctattatcgc cacacaaacg   360
acagcaatac ataatacgcc tcaacccaac gtaatatctg caatatcgga gttatttaca   420
gccattgccg aacacgggac agtattttta ctagtagcta atttcgattt ccgtcaatta   480
tctacatcat gaaaccactc ttacgatcgc acgaaacaca atactacagt ctgtatcctg   540
acacgctgaa cgg                                                     553

<210> SEQ ID NO 8
<211> LENGTH: 26
<212> TYPE: DNA
<213> ORGANISM: Marek's disease gammaherpesvirus

<400> SEQUENCE: 8
cccgtttgca tatgcaaaat tcatac                                       26

<210> SEQ ID NO 9
<211> LENGTH: 29
<212> TYPE: DNA
<213> ORGANISM: Marek's disease gammaherpesvirus

<400> SEQUENCE: 9
ggaacgttgt atcatcatac atgtgttcg                                    29

<210> SEQ ID NO 10
<211> LENGTH: 750
<212> TYPE: DNA
<213> ORGANISM: Marek's disease gammaherpesvirus

<400> SEQUENCE: 10
cccgtttgca tatgcaaaat tcatacatcc atatactccc atgatgaccc tcgcagtttt    60
taaatataac ctaaatagaa acctgaaatt atcacaagta ctacagttct gtcagatata   120
tcctaactcc taataacaaa gtacacgtga ataggcccta acagtgaaac gatatactcg   180
gttactacat taaaatatta atcggaatta cacttctgaa ggatctggtt catgtaaatc   240
ttaaccattc tatatagcaa tatacggatt ctatattgtc ttataaataa gtaaattgca   300
tgttttaacc tataattaac tcgttatagg tagacatgac tcatactagg gttgatttgc   360
acatagctta gccagatgca gtaaatatat tgtcacgtgg ctaaaacgtg agtagtaact   420
tatatggcga attaaactta tatccaatgg cgttcgcgga ccttcacacg gaaacatgtg   480
tggtgcgaca ttcaagtggt tatgagcgtc agttgaacgt agaacatgcg cattgcaatt   540
atgtcccaga atcctccccc atataaattc gtctactgaa attcaagagc acttgctgta   600

-continued

```
ttacttccac ttcgacgaac aacacacaag accagtcagc cgcgaacgga ataacgccg        660 aatcgagctc ctctaattcc gataaccggc tgttgtcaat ggcaggaata actatgggca       720
gcgaacacat gtatgatgat acaacgttcc                                        750
```

```
<210> SEQ ID NO 11
<211> LENGTH: 40
<212> TYPE: DNA
<213> ORGANISM: Artificial Sequence
<220> FEATURE:
<223> OTHER INFORMATION: DNA adapter

<400> SEQUENCE: 11 cggcccccccc ggcttttat ttatttaggt atgctggggg                              40
```

```
<210> SEQ ID NO 12
<211> LENGTH: 48
<212> TYPE: DNA
<213> ORGANISM: Artificial Sequence
<220> FEATURE:
<223> OTHER INFORMATION: DNA adapter

<400> SEQUENCE: 12
tcgaccccca gcatacctaa ataaataaaa agccgggggg gccggtac                     48
```

```
<210> SEQ ID NO 13
<211> LENGTH: 47
<212> TYPE: DNA
<213> ORGANISM: Artificial Sequence
<220> FEATURE:
<223> OTHER INFORMATION: DNA adapter

<400> SEQUENCE: 13
ggccgctaaa taaataaaaa ggccccccccg gccaccgcgg tggagct                     47
```

```
<210> SEQ ID NO 14
<211> LENGTH: 39
<212> TYPE: DNA
<213> ORGANISM: Artificial sequence
<220> FEATURE:
<223> OTHER INFORMATION: DNA adapter

<400> SEQUENCE: 14
ccaccgcggt ggccgggggg gccttttat ttatttagc                                39
```

```
<210> SEQ ID NO 15
<211> LENGTH: 58
<212> TYPE: DNA
<213> ORGANISM: Artificial Sequence
<220> FEATURE:
<223> OTHER INFORMATION: DNA adapter

<400> SEQUENCE: 15
catggagatc tattcgtact tggcggccag ctcctcgagt aattagttga ataatagc          58
```

```
<210> SEQ ID NO 16
<211> LENGTH: 58
<212> TYPE: DNA
<213> ORGANISM: Artificial Sequence
<220> FEATURE:
<223> OTHER INFORMATION: DNA adapter

<400> SEQUENCE: 16
ggccgctatt attcaactaa ttactcgagg agctggccgc caagtacgaa tagatctc          58
```

<210> SEQ ID NO 17
<211> LENGTH: 29
<212> TYPE: DNA
<213> ORGANISM: Artificial Sequence
<220> FEATURE:
<223> OTHER INFORMATION: PCR primer

<400> SEQUENCE: 17
cggtcgttac ggatcctatt attcaggca                               29

<210> SEQ ID NO 18
<211> LENGTH: 30
<212> TYPE: DNA
<213> ORGANISM: Artificial Sequence
<220> FEATURE:
<223> OTHER INFORMATION: PCR primer

<400> SEQUENCE: 18
gcgatcgtaa gagtccatgg atgatgtaga                              30

<210> SEQ ID NO 19
<211> LENGTH: 577
<212> TYPE: DNA
<213> ORGANISM: Artificial Sequence
<220> FEATURE:
<223> OTHER INFORMATION: Modified SEQ ID NO.7

<400> SEQUENCE: 19
ggtaccggcc cccccggctt tttatttatt taggtatgct gggggtcgac ggtatcgata    60
agcttgatat cgaattcctg cagcccgggg gatcctatta ttcaggcaac tatcgccaac   120
cctctgttct ccctagatgc gatcgatatt agaaagatct ataaaatgta atacggcttt   180
caataccaca actcctaaaa ccagtcgtga ttacgtagta tagtcatgcc catttcagag   240
aacatacaat aacacagtaa aatcctacta aatattgtat ctgcactatt acttgaccat   300
gccagagtaa atcgtcattt ctattatcgc cacacaaacg acagcaatac ataatacgcc   360
tcaacccaac gtaatatctg caatatcgga gttatttaca gccattgccg aacacgggac   420
agtattttta ctagtagcta atttcgattt ccgtcaatta tctacatcat ccatggagat   480
ctattcgtac ttggcggcca gctcctcgag taattagttg aataatagcg gccgctaaat   540
aaataaaaag gccccccccgg ccaccgcggt ggagctc                          577

<210> SEQ ID NO 20
<211> LENGTH: 30
<212> TYPE: DNA
<213> ORGANISM: Artificial Sequence
<220> FEATURE:
<223> OTHER INFORMATION: PCR primer

<400> SEQUENCE: 20
catccatata ggatcctatg atgaccctcg                              30

<210> SEQ ID NO 21
<211> LENGTH: 30
<212> TYPE: DNA
<213> ORGANISM: Artificial Sequence
<220> FEATURE:
<223> OTHER INFORMATION: PCR primer

<400> SEQUENCE: 21
cccatagtta ttccatggat tgacaacagc                              30

<210> SEQ ID NO 22
<211> LENGTH: 863
<212> TYPE: DNA
<213> ORGANISM: Artificial Sequence
<220> FEATURE:
<223> OTHER INFORMATION: Modified SEQ ID. NO.10

<400> SEQUENCE: 22

```
ggtaccggcc cccccggctt tttatttatt taggtatgct gggggtcgac ggtatcgata      60
agcttgatat cgaattcctg cagcccgggg gatcctatga tgaccctcgc agttttaaaa     120
tataacctaa atagaaacct gaaattatca caagtactac agttctgtca gatatatcct     180
aactcctaat aacaaagtac acgtgaaata ggcctaacag tgaaacgata tactcggtta     240
ctacattaaa atattaatcg gaattacact tctgaaggat ctggttcatg taaatcttaa     300
ccattctata tagcaatata cggattctat attgtcttat aaataagtaa attgcatgtt     360
ttaacctata attaactcgt tataggtaga catgactcat actagggttg atttgcacat     420
agcttagcca gatgcagtaa atatattgtc acgtggctaa acgtgagta gtaacttata     480
tggcgaatta aacttatatc caatggcgtt cgcggacctt cacacggaaa catgtgtggt     540
gcgacattca agtggttatg agcgtcagtt gaacgtagaa catgcgcatt gcaattatgt     600
cccagaatcc tcccccatat aaattcgtct actgaaattc aagagcactt gctgtattac     660
ttccacttcg acgaacaaca cacaagacca gtcagccgcg aacggaaata acgccgaatc     720
gagctcctct aattccgata accggctgtt gtcaatccat ggagatctat tcgtacttgg     780
cggccagctc ctcgagtaat tagttgaata atagcggccg ctaaataaat aaaaaggccc     840
ccccggccac cgcggtggag ctc                                             863
```

<210> SEQ ID NO 23
<211> LENGTH: 30
<212> TYPE: DNA
<213> ORGANISM: Artificial Sequence
<220> FEATURE:
<223> OTHER INFORMATION: PCR primer

<400> SEQUENCE: 23

```
gggtaccggt agaaatcatg agtaaaggag                                       30
```

<210> SEQ ID NO 24
<211> LENGTH: 30
<212> TYPE: DNA
<213> ORGANISM: Artificial Sequence
<220> FEATURE:
<223> OTHER INFORMATION: PCR primer

<400> SEQUENCE: 24

```
cagttggaat tcgtcgactg ctatttgtat                                       30
```

<210> SEQ ID NO 25
<211> LENGTH: 30
<212> TYPE: DNA
<213> ORGANISM: Artificial Sequence
<220> FEATURE:
<223> OTHER INFORMATION: PCR primer

<400> SEQUENCE: 25

```
gcttgtcgac tctatcatga caaacctgtc                                       30
```

<210> SEQ ID NO 26
<211> LENGTH: 29
<212> TYPE: DNA

<210> SEQ ID NO 26
<211> LENGTH: 29
<212> TYPE: DNA
<213> ORGANISM: Artificial Sequence
<220> FEATURE:
<223> OTHER INFORMATION: PCR primer

<400> SEQUENCE: 26
ctgaaatgag cctcgagact gtgaatcta                                29

<210> SEQ ID NO 27
<211> LENGTH: 29
<212> TYPE: DNA
<213> ORGANISM: Artificial Sequence
<220> FEATURE:
<223> OTHER INFORMATION: PCR primer

<400> SEQUENCE: 27
gggttatagt tgcatgcgcg tggccggga                                29

<210> SEQ ID NO 28
<211> LENGTH: 28
<212> TYPE: DNA
<213> ORGANISM: Artificial Sequence
<220> FEATURE:
<223> OTHER INFORMATION: PCR primer

<400> SEQUENCE: 28 catgggggc tctcgagtgc agcataaa                                  28

<210> SEQ ID NO 29
<211> LENGTH: 30
<212> TYPE: DNA
<213> ORGANISM: Artificial Sequence
<220> FEATURE:
<223> OTHER INFORMATION: PCR primer

<400> SEQUENCE: 29 ggccggggggg gccgttagag gtgcgttttt                              30

<210> SEQ ID NO 30
<211> LENGTH: 30
<212> TYPE: DNA
<213> ORGANISM: Artificial Sequence
<220> FEATURE:
<223> OTHER INFORMATION: PCR primer

<400> SEQUENCE: 30 ccccccggc cttactgtgt tttatttatc                                30

<210> SEQ ID NO 31
<211> LENGTH: 24
<212> TYPE: DNA
<213> ORGANISM: Artificial Sequence
<220> FEATURE:
<223> OTHER INFORMATION: Primer of PCR products for Southern
      hybridyzation probe

<400> SEQUENCE: 31
caccgtcctc agcttaccca catc                                     24

<210> SEQ ID NO 32
<211> LENGTH: 23
<212> TYPE: DNA
<213> ORGANISM: Artificial Sequence
<220> FEATURE:
<223> OTHER INFORMATION: Primer of PCR products for Southern
      hybridyzation probe

<400> SEQUENCE: 32

```
acgacggatc ctgttgccac tct                                                23

<210> SEQ ID NO 33
<211> LENGTH: 24
<212> TYPE: DNA
<213> ORGANISM: Artificial Sequence
<220> FEATURE:
<223> OTHER INFORMATION: Primer of PCR products for Southern
      hybridyzation probe

<400> SEQUENCE: 33
ggggaagtct tccggttaag ggac                                               24

<210> SEQ ID NO 34
<211> LENGTH: 24
<212> TYPE: DNA
<213> ORGANISM: Artificial Sequence
<220> FEATURE:
<223> OTHER INFORMATION: Primer of PCR products for Southern
      hybridyzation probe

<400> SEQUENCE: 34
ggtgcaattc gtaagaccga tggg                                               24
```